United States Patent [19]

Halsør et al.

[11] Patent Number: 4,480,928

[45] Date of Patent: Nov. 6, 1984

[54] METHODS OF FLAW DETECTION IN BILLETS

[75] Inventors: Svein R. Halsør, Bjørkås; Magnar K. Storset, Hosle, both of Norway

[73] Assignee: Elkem a/s, Oslo, Norway

[21] Appl. No.: 437,251

[22] Filed: Oct. 28, 1982

[30] Foreign Application Priority Data

Nov. 3, 1981 [NO] Norway ................ 813705

[51] Int. Cl.³ ........................ G01N 25/72
[52] U.S. Cl. ........................ 374/5; 374/57
[58] Field of Search ............. 374/4, 5, 9, 7, 32

[56] References Cited

U.S. PATENT DOCUMENTS

| | | | |
|---|---|---|---|
| 3,020,745 | 2/1962 | Sielicki | 374/5 |
| 3,378,685 | 4/1968 | Green et al. | 374/5 X |
| 3,945,245 | 3/1976 | Stehle et al. | 374/9 X |
| 4,109,508 | 8/1978 | Fukuyama | 374/5 |

Primary Examiner—Daniel M. Yasich
Attorney, Agent, or Firm—Lucas & Just

[57] ABSTRACT

Cracks and surface flaws in billets are detected by heating the surface of the work-piece by means of high frequency current, the heating taking place while the work-piece is brought to pass in its longitudinal direction through a high frequency induction coil. That part of the work-piece, which has just left the coil is immediately, while the work-piece is still passing through the coil, scanned by means of infrared recording equipment which records the temperature distribution across the work-piece. The emission coefficient for the different work-pieces is increased and differences equalized by moistening the surface of the work-piece with an appropriate liquid, for instance water, to which have been added components for reduction of the surface tension.

5 Claims, 3 Drawing Figures

EMISSION CONDITIONS FOR DIFFERENT WORKPIECE SURFACES, WET AND DRY
THE SURFACES ARE RELATED TO SIS 055900-1967
(WORKPIECE NOS IN BRACKETS)

| A (AA7 B) | | | | B (102 B) | | | | CSa 1-2 (66A) | | | | CSa 2 (27B) | | | | CSa 2½ (60B) | | | |
|---|---|---|---|---|---|---|---|---|---|---|---|---|---|---|---|---|---|---|---|
| DRY | | WET | | DRY | | WET | | DRY | | WET | | DRY | | WET | | DRY | | WET | |
| T | IR | T | IR | T | IR | T | IR | T | IR | T | IR | T | IR | T | IR | T | IR | T | IR |
| 23.9 | 21.0 | 22.4 | 19.0 | 24.1 | 20.0 | 22.3 | 18.0 | 22.7 | 19.5 | 21.9 | 18.5 | 23.4 | 20.0 | 22.3 | 18.5 | 22.4 | 19.0 | 22.0 | 18.5 |
| 25.8 | 23.0 | 24.7 | 22.0 | 25.4 | 21.5 | 26.1 | 22.5 | 25.1 | 21.0 | 25.3 | 22.5 | 26.6 | 21.0 | 25.0 | 22.5 | 24.9 | 20.0 | 25.4 | 23.0 |
| 30.7 | 28.5 | 29.7 | 27.5 | 30.1 | 27.0 | 30.2 | 27.5 | 30.1 | 24.0 | 30.0 | 27.5 | 29.8 | 22.5 | 29.7 | 27.5 | 30.0 | 22.0 | 31.4 | 29.5 |
| 35.6 | 34.0 | 36.7 | 35.5 | 35.5 | 33.5 | 35.6 | 33.5 | 35.0 | 27.5 | 34.5 | 32.5 | 34.8 | 24.5 | 35.8 | 34.5 | 35.0 | 24.0 | 34.7 | 33.0 |
| 40.4 | 38.0 | 41.3 | 40.0 | 40.1 | 38.0 | 40.0 | 38.5 | 40.0 | 30.5 | 40.0 | 38.5 | 39.4 | 26.5 | 40.0 | 38.5 | 40.0 | 26.0 | 40.0 | 38.0 |
| 47.7 | 45.0 | 47.2 | 45.5 | 46.0 | 45.0 | 44.6 | 43.5 | 44.3 | 34.5 | 45.3 | 44.0 | 45.7 | 29.0 | 46.0 | 45.0 | 45.8 | 28.0 | 44.7 | 42.5 |
| 50.0 | 47.0 | | | 50.1 | 48.0 | | | | | | | | | | | | | | |

T = TEMPERATURE RECORDED BY CONTACTPYROMETRE
IR = TEMPERATURE RECORDED BY IR EMISSIONPYROMETRE

FIG.1

METHODS OF FLAW DETECTION IN BILLETS

The invention relates to a method for detecting of billets, that is indication of a surface cracks or flaws in the billet so that these can be indicated and removed for instance by grinding of the billet, so that the flaws will not follow the workpiece in the further production process to finished products.

It is known that cracks and surface flaws in billets can be detected by heating the surface of the workpiece by means of high frequency current while the workpiece is brought to pass in its longitudinal direction through a high frequency induction coil, that part of the workpiece which has just left the coil, being, while the workpiece is passing through the coil, immediately scanned by means of an infrared recording equipment for recording of the temperature distribution across the workpiece. The temperature distribution is recorded and shown as a streaked pattern which indicates cracks and surface flaws in the billet. By such recording of the temperature profile across the workpiece along one scanning, there will be found an increase of temperature in the temperature profile adjacent the cracks. The temperature increases which are repeated from scanning to scanning, will when they are combined, form a temperature ridge along the workpiece which ridge then indicates a crack in the workpiece. The present invention aims at such recording of very shallow surface flaws (less than 1 mm deep) and at obtaining uniform emission conditions for all surfaces and simultaneously reducing the disturbances in the temperature picture.

It has in connection with the described method for detecting of workpieces proved that there by temperature measurements with infrared scanner (IR emission pyrometer) is obtained temperatures which deviate from the real temperature of the surface because of the emission coefficient of the surface. The emission coefficient is depending on the nature of the surface and will vary between 0 and 1. Rolled workpieces with mill scale will usually have an emission coefficient of about 0.90–0.95.

In order to obtain the best conditions during the detection of the workpieces, and thereby as few disturbances as possible in the temperature picture it is desirable to have a surface which is so clean as possible. This can for instance be obtained by means of shot blasting of the surface, and the degree of purification can for instance be classified according to the Swedish standard, SIS 055990/1967. By such shot blasting there is, however, also obtained the undesired secondary effect that the surface becomes bright and its emission conditions are altered. This will again effect the temperature, which is recorded on the IR emission pyrometer, so that temperature measurements with IR emission pyrometer will give too low surface temperature, so that a too low temperature in the cracks is recorded. These results in that there by a shot blasted workpieces will occur a reduction of the recorded super-temperature in the cracks in relation to the workpieces with mill scale, and which again results in different interpretation of the depth of the cracks, depending on the emission coefficient of the surface. This is an undesirable condition, which complicates the use of the method, as one in order to obtain correct results must recalibrate the equipment for each new type of surface. This requires much time, and is complicated and not appropriate for industrial operation.

The inventors have, however, now found that the emission coefficient for all types of workpiece surfaces can be made approximately equal by moistening of the surface with an appropriate liquid, for instance water to which have been added components, which effects a decrease of the surface tension, so that a better moistening is obtained. By detection of workpieces at temperatures below 0° C. components which decrease the freezing temperature can also be added. Experiments have shown that there by such moistening of the surface of the workpiece with water to which have been added components for decreasing the surface tension is obtained that all workpiece surfaces, independent of the pretreatment will have approximately same emission coefficient, and these emission coefficient will deviate only to a small degree from the emission coefficient for a dry workpiece with mill scale. The variation in the emission coefficient for moistened workpieces is so small that it has no practical importance for the result of the above described detection method. By moistening for the workpieces were also obtained less disturbances in the temperature picture, as the differences in emission coefficient for different areas of the surface will be equalized, and there is obtained an important improvement of the signal/disturbance ratio in the signals from IR emission pyrometer. By shot blasted workpieces, which have not been moistened, the signal/disturbance ratio is so low there by certain types of workpiece surfaces will arise problems with detection of the most shallow cracks.

FIG. 1 is a compilation table of temperature measurements with contact pyrometer and IR emission pyrometer for different types of workpiece surfaces, wet as well as dry.

Figure 3:
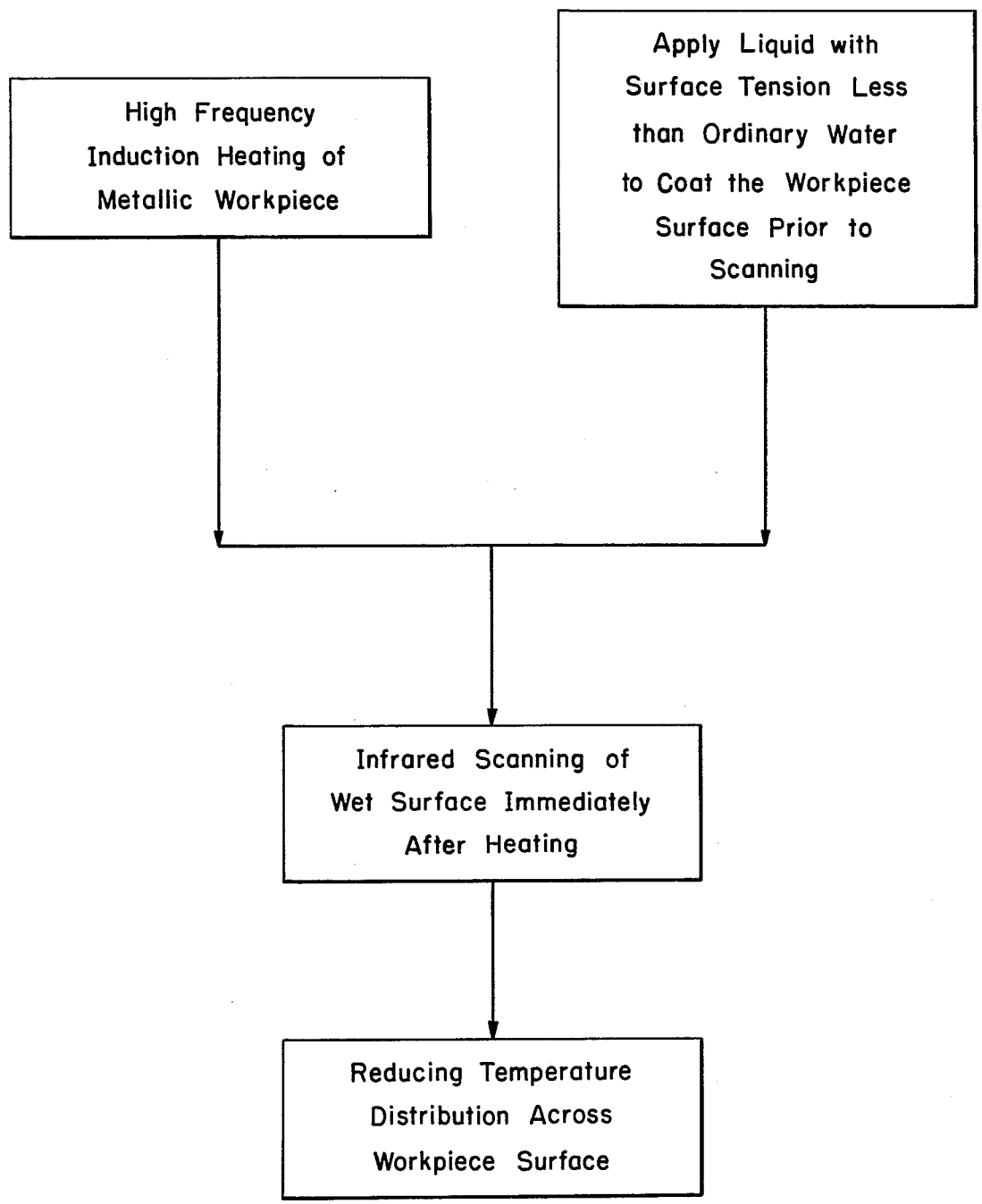

FIG. 3 schematically illustrates the steps on one preferred method of carrying out the present invention for determining flaws in a metallic workpiece.

Sample A of the table of FIG. 1 relates to a workpiece with mill-scale. Sample B relates to a workpiece with corroded (rusted) surface, while the samples marked CSa 1-2; CSa 2 and CSa 2½ are cleaned by shot blasting, and the surfaces are defined in accordance with Swedish standard SIS 055900-1967.

In the table T means temperature read by contact pyrometer, while IR shows temperatures read by IR emission pyrometer. As mentioned the readings are carried out as well on dry as on moistened surface.

A shown by the columns "dry" there is an important temperature deviation between the two measurements and this deviation increases with the degree of shot blasting, which is here designated respectively as CSa 1-2 CSa2 and CSa 2½. The deviation between the two principles of measurement is thus increasing with the brightness of the workpiece. This carries with it that there by measurements with IR emission pyrometer for shot blasted workpieces is recorded too low workpiece temperature and consequently a lower increase of temperature in the scale. These facts can as mentioned have as a result that one in order to obtain acceptable results must calibrate the equipment in dependency of the emission coefficient of the surface, and this is an important drawback as the emission coefficient can vary from workpiece to workpiece.

Reduction of the temperature tops at the cracks for shot blasted surfaces will also have as result that there is operated with less tolerances between the temperature tops at the flaws, and temperatures for flawless surface, so that is there is obtained an reduced signal/disturbance ratio which is unfavourable.

Tests have as mentioned above shown that the emission coefficient for different workpiece surfaces can be altered, and made approximately equal for all surfaces by moistening of the surface. By approximately equal is meant that the emission coefficients of the workpiece surfaces are within an area which can be accepted for the results of the detection method. The workpiece can be moistened before it passes through the induction coil, and the moistening liquid is supplied as uniformly as possible on the surface, either through a nozzle, slot or similar arrangement or by letting it flow down along the surface. The effect of these moistening is shown by the table in the columns marked "wet".

Figure 2:
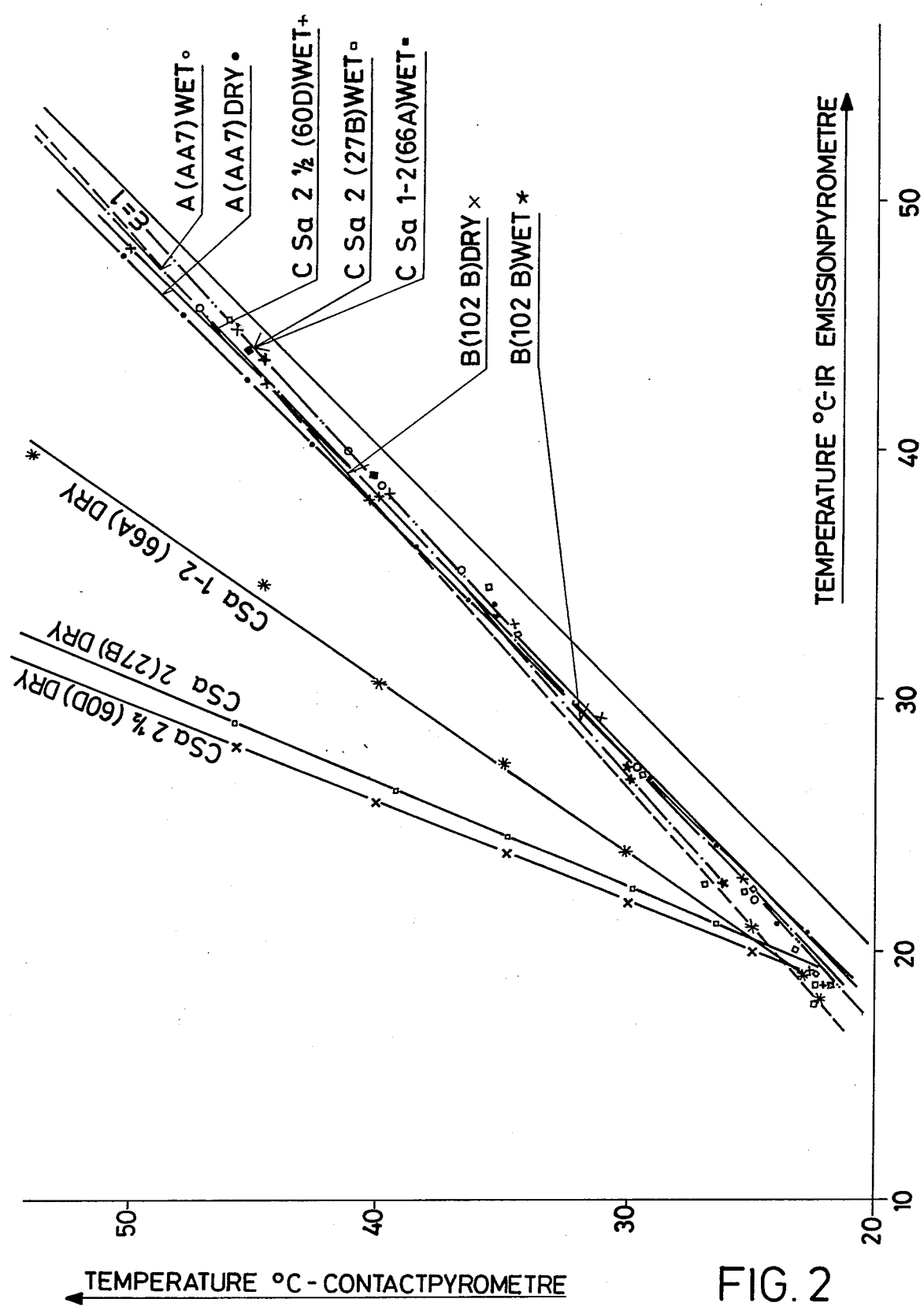
FIG. 2 is a graph of the dry and wet surface temperatures of the table of FIG. 1.

The results from measurements for "dry" and "wet" surface as indicated in the table is also represented graphically in appended FIG. 2. As seen from these diagrams the emission coefficient for moistened surfaces are all on the same level as for dry workpiece with mill-scale, workpiece A (A A7B). It is further seen that there by moistening is obtained that all surfaces have approximately the same emission coefficient, which are positioned relatively close to the theoretical maximum emission coefficient which is 1.

As mentioned there is by moistening of the workpiece also obtained the advantage that the disturbance level for flawless surface defined as temperature variations across the surface is reduced simultaneously as the temperature increase in connection with a flaw defined as super temperature across flawless surface is increased, which means that the ratio signal/disturbance is improved.

We claim:

1. In the method of detecting flaws in the surface of metal workpieces which are heated by a high frequency current induction heater and scanned by infrared equipment to record the temperature disturbance across the surface of the workpiece and thereby indicate surface flaws by heat emitted from the surface, the improvement which comprises the steps of:
   (a) passing the metal workpiece in longitudinal direction through a high frequency induction heater;
   (b) immediately scanning the surface of the workpiece with infrared equipment to record the temperature distribution across the workpiece as it passes from said heater; and
   (c) prior to said immediate scanning, applying to the surface of the workpiece water having surface tension below that of ordinary water and of sufficiently low surface tension to wet and coat the surface of the workpiece to be inspected by scanning and thereby change the emission coefficient and compensate for differences in the characteristics of workpiece surfaces.

2. The method of claim 1 in which said water has a freezing point below the freezing point of ordinary water.

3. In the method of detecting flaws in the surface of metal billets which are heated by high frequency induction heating and scanned by infrared equipment to record the temperature disturbance across the surface of the billet and thereby indicate surface flaws by heat emitted from the surface, the improvement which comprises the steps of:
   (a) passing the metal billet in longitudinal direction through a high frequency induction coil;
   (b) immediately scanning the surface of the billet with infrared equipment to record the temperature distribution across the surface of the billet as it passes from said coil; and
   (c) prior to said immediate scanning, coating the surface of billet with a liquid selected to have surface tension characteristics below that of ordinary water necessary to wet the surface of the metal billet to be inspected by scanning and thereby change the emission coefficient of the surface of the metal billet and compensate for differences in the characteristics of billet surfaces.

4. The method of claim 3 in which the metal billet is pretreated to brighten the surface prior to said high frequency induction heating.

5. The method of claim 3 which includes the step of shot blasting the surface of the billet prior to said high frequency induction heating.

* * * * *